US00PP25765P2

(12) United States Plant Patent
Friday

(10) Patent No.: US PP25,765 P2
(45) Date of Patent: Aug. 4, 2015

(54) PEACH TREE NAMED 'P.F. LEGENDARY'

(50) Latin Name: *Prunus persica*
Varietal Denomination: P.F. Legendary

(71) Applicant: Paul Jan Friday, Coloma, MI (US)

(72) Inventor: Paul Jan Friday, Coloma, MI (US)

( * ) Notice: Subject to any disclaimer, the term of this patent is extended or adjusted under 35 U.S.C. 154(b) by 72 days.

(21) Appl. No.: 13/573,991

(22) Filed: Oct. 19, 2012

(51) Int. Cl.
*A01H 5/08* (2006.01)

(52) U.S. Cl.
USPC ..... Plt./198

(58) Field of Classification Search
USPC ..... Plt./198
CPC ..... A01H 5/0868; A01H 5/0837
See application file for complete search history.

*Primary Examiner* — Susan McCormick Ewoldt

(57) ABSTRACT

A new and distinct variety of peach, *Prunus persica*, tree having the following unique combination of desirable features.

1. The new and distinct variety of peach tree is of average height and of upright growth and a regular and productive bearer of peaches.
2. Producing a very firm fruit having a resilient flesh texture.
3. Blossoms are non-showy when in full bloom.
4. A substantially spherical fruit with skin of red color (70-75%) overlying yellow at the maturity of the fruit.
5. A late maturing fruit of good taste.
6. A late maturing fruit of good storage and shelf life.

1 Drawing Sheet

Botanical classification: *Prunus persica.*

ORIGIN OF VARIETY

The new peach tree (hereinafter referred to as the 'P.F. Legendary ') was originated by Paul Friday in the experimental orchard, which is maintained for the purposes of breeding peach trees, located in Coloma, Mich. Coloma is located in the southwest section of Michigan, USDA Hardiness Zone 6A, with observed temperature ranges of minus 12 degree Fahrenheit to 90 degree Fahrenheit, also with annual rainfall of about 40 inches.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for there adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application, 'P.F. Legendary', of unknown parents, was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in an experimental orchard located in Coloma, Mich. The asexual propagation demonstrates that such reproduction of the characteristics of the tree are consistent and are established and transmitted through succeeding asexual propagation.

SUMMARY OF THE VARIETY

The new and very distinct variety of peach tree is of average height and of upright growth and a regular and productive bearer of peaches. A distinguishing characteristic is that it is a late maturing peach, 41 days after 'Redhaven' (non-patented) in southwest Michigan. The blossoms are characterized as being non-showy. More specifically the blossoms of 'P.F. Legendary' peach tree have angularly spaced five-blossom petals projecting upwardly at an inclined angle so as to form a blossom, having about 1" diameter, measured across the blossoms in full bloom. At the same time petals of blossoms are of lesser length than length of petals of normal showy blossom as exemplified by 'Loring' (non-patented) peach.

The fruit at maturity is large, having flesh that is firm and a dark yellow with red around the pit cavity.

The skin is smooth with notably little down and is of red overlying yellow ground color. The yellow background covers approximately twenty five percent (25%) of its surface at maturity. At maturity, the peach is notably well rounded having an average diameter of about 2¾".

The fruit produced by this tree has firm, and non-melting flesh, and thereby has the attendant resistance to blemishes and soft spots in harvesting, shipping and handling due to bruising. The firmness of the fruit flesh is sufficient to allow the flesh to yield and be restored when bumped or dropped without the resulting soft spots as would be experienced in most late season peaches of the market class. Thus, fruit of this tree remains more attractive to the ultimate buyer, the consumer, and thereby will command premium prices for late fresh desert market.

The fruit matures very late 41 days after 'Redhaven' (non-patented) peach in southwestern Michigan, it stores very well in a refrigerated room at 33 degree Fahrenheit for up to 3 weeks without becoming dry or mealy, remaining very sweet 12 brix of sugar. The fruit as mentioned heretofore is of red overlying yellow which covers approximately twenty five (25%) of its surface and has a very attractive appearance.

BRIEF DESCRIPTION OF THE PHOTOGRAPHS

In the accompanying drawing the top photograph shows the leaves of the 12 yr old plant depicting both upper and lower sides. A tape measure is included showing the length of a leaf.

The bottom photograph shows three (3) whole fruits with one bisected across the axis showing that it is freestone, and has a clear yellow flesh with red around the pit. A tape measure has been placed in the photograph showing that the fruit form this tree has the genetic capability to exceed two and three-quarters inches (2¾") in diameter.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panton Matching System (PMS) as used internationally to identify printed colors.

Botanical classification: *Prunus persica* cultivar 'P.F. Legendary'.

Tree:
- *Age*.—Twelve (12) years.
- *Height*.—Unpruned 14'.
- *Width*.—Unpruned 8'.
- *Size*.—Large.
- *Vigor*.—vigorous.
- *Density*.—Medium — moderate pruning required.
- *Form*.—Upright.
- *Production*.—Very good — sizes well with a minimum amount of thinning.
- *Bearer*.—Consistent.
- *Disease resistance to bacterial leaf spot and fruit spot*.—Very resistant.
- *Rootstock*.—Grown on its own roots.

Trunk:
- *Bark*.—Gray (Panton # 409).
- *Size*.—Medium.
- *Surface*.—Rough.
- *Diameter*.—4½" diameter at 12" above ground at 5 years of age.
- *Lenticels*.—Not pronounced.
- *Lenticels color*.—#132.
- *Lenticels size*.—3/16".

Branches:
- *Size*.—2½" diameter at 10" from trunk.
- *Surface*.—Semi-smooth — Lenticels are more pronounced on under side of branch.
- *Lenticels per square inch*.—Six (6).
- *Lenticels color*.—#131.
- *Lenticels size*.—⅛".
- *Crotch angles*.—60 degree angles.
- *Branch color*.—#436.
- *Internodes length*.—⅝"-1½".

Leaves:
- *Size*.—Average length 6⅛", Average width 1½".
- *Form*.—Lanceolate — pointed.
- *Thickness*.—Medium.
- *Margin*.—Serrated.
- *Leaf base shape*.—Acute.
- *Leaf apex shape*.—Pointed.
- *Petiole length*.—⅜".
- *Gland shape*.—Oval.
- *Gland color*.—Brown (#174).
- *Gland number*.—2-4 mostly on petiole occasionally one on leaf.
- *Leaf color*.—Adaxial (Top) or upper leaf surface green #350.
- *Leaf color*.—Abaxial (Bottom) or bottom leaf surface #363.

Flower buds:
- *Size*.—½" long — ¼" wide.
- *Bud shape*.—Ovate.
- *Bud color*.—Panton # 205.

Flowers:
- *Blooming period*.—May 5, 2011 thru May 12, 2011.
- *Bloom size*.—1" diameter.
- *Bloom depth*.—⅜" deep at full maturity.
- *Size of petals*.—½" long — ⅜" wide.
- *Shape of petals*.—Slightly cupped.
- *Petal margins*.—Entire (smooth).
- *Petal base shape*.—Pointed.
- *Petal apex shape*.—Ovate.
- *Petal color*.—Top — pink (pantone# 218).
- *Number of petals*.—Five (5).
- *Sepal size*.—9/32" long — 3/32" wide.
- *Sepal shape*.—Very slightly cupped.
- *Sepal apex*.—Pointed.
- *Sepal base*.—Flat.
- *Sepal color*.—Pantone # 201.
- *Number of sepals*.—Five (5).
- *Number of anthers*.—Twenty four (24).
- *Anthers color*.—Pantone # 160.
- *Number of stamens*.—Twenty four (24).
- *Stamen length*.—⅜".
- *Stamen color*.—Pantone # 214 stamens changed color at maturity to a white or clear.
- *Pistil length*.—½" pistil is long & bent on end.
- *Pistil color*.—Pantone #101.
- *Pollen*.—Self-pollinating.
- *Flower color*.—Pink Pantone # 218.
- *Number flowers per cluster*.—Two (2).
- *Fragrance*.—Very fragrant.

Fruit:
- *Maturity when described*.—Firm ripe.
- *Date of first picking*.—Normally September 16 in Southwestern Michigan.
- *Date of last picking*.—September 22 in Southwestern Michigan.
- *Size*.—Average 2¾".
- *Form*.—Spherical.
- *Suture*.—Minimal.
- *Weight*.—7 oz.

Skin:
- *Thickness*.—Medium as compared to the species.
- *Texture*.—Medium as compared to the species.
- *Tendency to crack*.—None.
- *Down*.—Light (short as compared to the species).

*Color*.—About 70-75% Red (Pantone # 179) over yellow ground color (Pantone # 121).

Flesh:

*Texture*.—Firm — non-melting, free of fiber.

*Ripens*.—Evenly.

*Flavor*.—Very good (sweet).

*Aroma*.—Pleasant.

*Eating quality*.—Excellent.

*Brix*.—Average of 12%.

*Color*.—Yellow (Pantone # 106).

*Pit cavity color*.—Red (Pantone # 186).

Stone:

*Type*.—Freestone.

*Size*.—1 9/16" long 1 1/8" wide 5/8" thick.

*Form*.—Ovate.

*Base*.—Flat.

*Apex*.—Pointed.

*Sides*.—Even.

*Surface*.—Furrowed.

*Color*.—Reddish brown #160.

*Tendency to crack*.—None.

*Kernel*.—3/4" long — 1/2" wide — 1/4" thick.

*Kernel taste*.—Bland.

Use: Dessert.

Shipping quality: Very good.

Keeping quality: Very good (up to three (3) weeks).

Disease resistance: The fruit is resistant to brown rot.

The tree and its fruit herein described may vary slightly as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

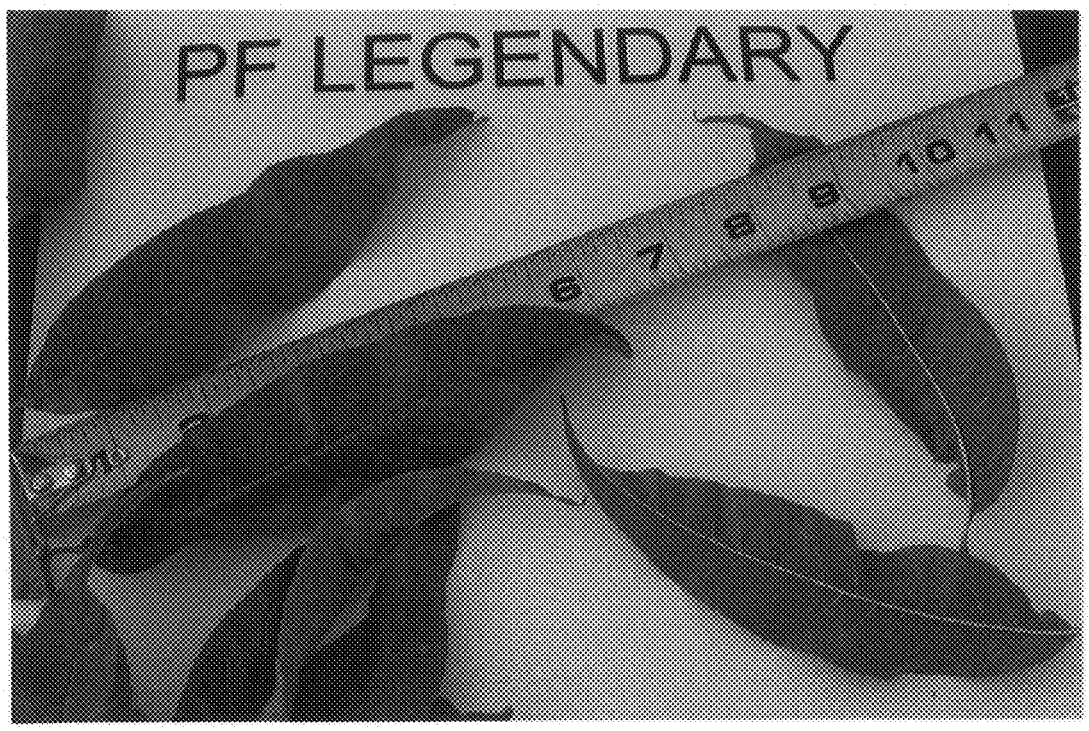
PF LEGENDARY
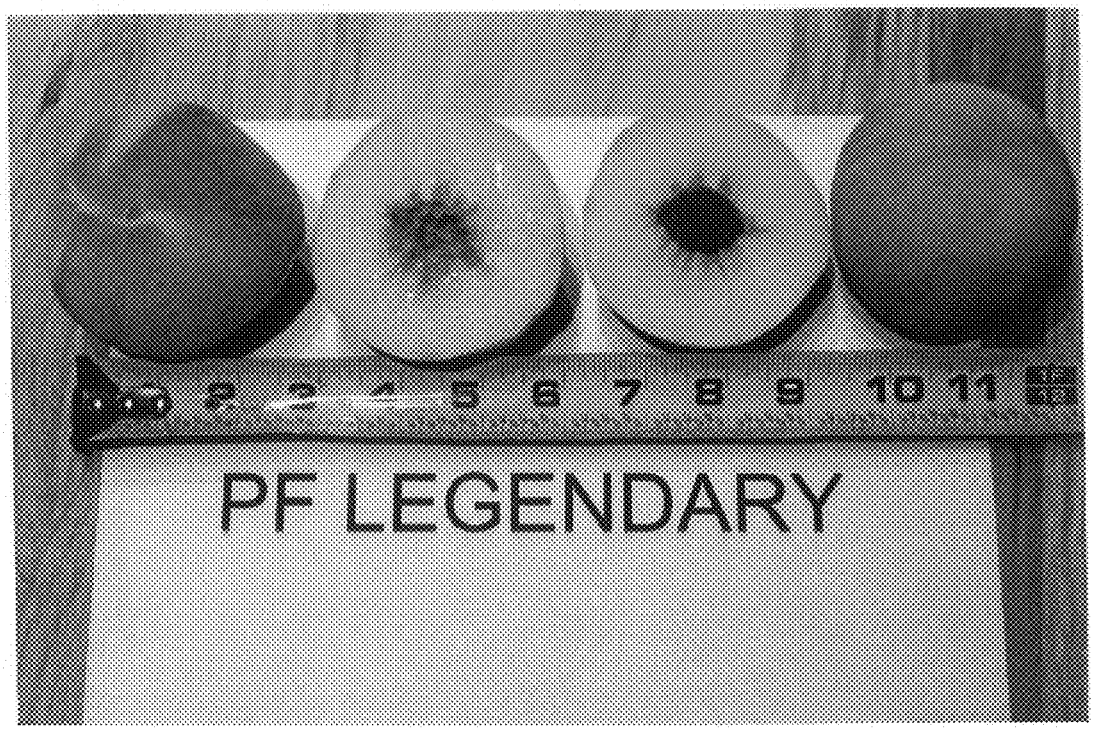
PF LEGENDARY